(12) United States Patent
Choi

(10) Patent No.: US 7,227,143 B2
(45) Date of Patent: Jun. 5, 2007

(54) X-RAY DETECTING DEVICES AND APPARATUS FOR ANALYZING A SAMPLE USING THE SAME

(75) Inventor: Kyung-Duk Choi, Gyeonggi-do (KR)

(73) Assignee: Dongbu Electronics Co., Ltd., Seoul (KR)

( * ) Notice: Subject to any disclaimer, the term of this patent is extended or adjusted under 35 U.S.C. 154(b) by 0 days.

(21) Appl. No.: 11/214,116

(22) Filed: Aug. 29, 2005

(65) Prior Publication Data

US 2006/0138325 A1  Jun. 29, 2006

(30) Foreign Application Priority Data

Dec. 29, 2004  (KR) .................. 10-2004-0115296

(51) Int. Cl.
*G21K 7/00* (2006.01)
*G01N 23/223* (2006.01)
(52) U.S. Cl. .................. 250/310; 250/306; 378/70; 378/98.8
(58) Field of Classification Search .................. None
See application file for complete search history.

(56) References Cited

U.S. PATENT DOCUMENTS

| 5,345,491 A * | 9/1994 | Bolk et al. ................... 378/70 |
| 5,903,004 A * | 5/1999 | Koshihara et al. .......... 250/310 |
| 6,479,818 B1 * | 11/2002 | McCarthy et al. .......... 250/310 |

\* cited by examiner

*Primary Examiner*—Nikita Wells
(74) *Attorney, Agent, or Firm*—Andrew D. Fortney

(57) ABSTRACT

X-ray detecting devices and apparatus for analyzing a sample using the same are disclosed. A disclosed X-ray detecting device has an X-ray detector to detect X-rays emitted from a sample. The X-ray detector includes a collimator to collimate the X-rays, an electron trap to remove electrons included in the collimated X-rays, a window to transmit the X-rays and defining an interior space of the X-ray detector, a crystal to receive the X-rays which pass through the window and to generate a corresponding electric current, a field effect transistor to generate a signal in response to the electric current, and a vacuum pump to create a vacuum within the interior of the X-ray detector containing the field effect transistor and the crystal to suppress noise associated with at least one of the crystal and/or the field effect transistor.

3 Claims, 5 Drawing Sheets

X-RAY DETECTING DEVICES AND APPARATUS FOR ANALYZING A SAMPLE USING THE SAME

FIELD OF THE DISCLOSURE

The present disclosure relates generally to X-ray detecting devices and apparatus for analyzing a sample using the same, and, more particularly, to X-ray detecting devices for detecting X-rays emitted from a sample so as to perform a compositional analysis, and analyzing apparatus combining a scanning electron microscope and an X-ray detector so as to perform a structural analysis and compositional analysis together.

BACKGROUND

An X-ray detector is an apparatus, for example one used for EDX (Energy Dispersive X-ray Spectroscopy), used for qualitative analysis such as for examining the compositional analysis of a sample.

When an electron collides with the sample, various kinds of electrons, ions, characteristic X-rays, etc., are emitted. An X-ray detector, such as an EDX, detects the emitted characteristic X-rays and expresses them according to the energy band of a beam. The characteristic X-rays have a magnitude that is energy-specific for each material. Therefore, a computer analyzes the material by comparing the magnitude of energy with pre-stored values of the magnitudes of energies for various materials.

These days, X-ray detectors and scanning electron microscopes are frequently used together. A scanning electron microscope may be used to perform a structural analysis of a sample. The scanning electron microscope scans electrons to perform this structural analysis. X-rays are generated by collision of the scanning electrons on the sample. These X-rays may be collimated by an X-ray detector. Therefore, when the scanning electron microscope and the X-ray detector are combined, structural analysis and compositional analysis may be performed at the same time.

FIG. 1A is a schematic diagram of a conventional EDX. Referring to FIG. 1A, a conventional EDX includes a cryo compressor 101, a filter 103, an isolation block 105, a cooler head 107, a manual valve 109, an electrical isolator 111, a main chamber 113, an X-ray detector 100, an I/O panel 115, and an EDX rack 117. Among the components of the conventional EDX, the X-ray detector 100 will be described hereinafter, with reference to FIG. 1B.

FIG. 1B shows a typical structure of a conventional X-ray detector 100. As shown in FIG. 1B, the conventional X-ray detector includes an X-ray collimator 120 for collimating the X-ray, an electron trap 130 for eliminating electrons from the collimated X-ray, a window 140 for transmitting the X-ray and sealing an interior of the X-ray detector so as to vacuumize the interior of the X-ray detector 100, a crystal 150 for generating an electric current corresponding to the energy of the X-ray, and a field effect transistor (FET) 160 for generating a voltage signal corresponding to the electric current generated by the crystal 150.

Since the crystal 150 and the FET (which are main parts of the X-ray detector) produce substantial noise at high temperatures, the crystal 150 and the FET are cooled to reduce the noise, and the X-ray detector 100 is sealed and maintained in a vacuum state. A vacuum is created within the interior of the X-ray detector to prevent contamination therein, oxidation of a filament, electric discharge, etc.

The noise produced by the crystal 150 decreases as the temperature thereof becomes lower. However, the noise of the FET only decreases until a certain temperature is reached; then, as the temperature becomes excessively low, the noise associated with the FET rises again. Therefore, an appropriate temperature must be maintained by a heater. Although not shown in the accompanying drawings, a heater is provided in the X-ray detector and is controlled by an external control module.

The inside of the X-ray detector 100 is cooled by liquid nitrogen ($LN_2$). To this end, a cryostat 200 is provided. The cryostat 200 is connected to an X-ray detecting device including the X-ray detector 100.

The liquid nitrogen is contained in the cryostat 200 and is usually consumed at a rate of about 1.1–1.3 liters a day.

Therefore, liquid nitrogen is periodically supplemented from a liquid nitrogen tank 300. The liquid nitrogen supplemented from the liquid nitrogen tank 300 to the cryostat 200 passes through a filter to prevent the inflow of foreign particles.

As described above, since the conventional X-ray detector 100 is used while being connected to the cryostat 200, various inconveniences including the periodic or aperiodic supplement of the liquid nitrogen and replacement of the filter occur.

In addition, since these are consumables, the maintenance cost is increased.

DETAILED DESCRIPTION

Figure 2A:
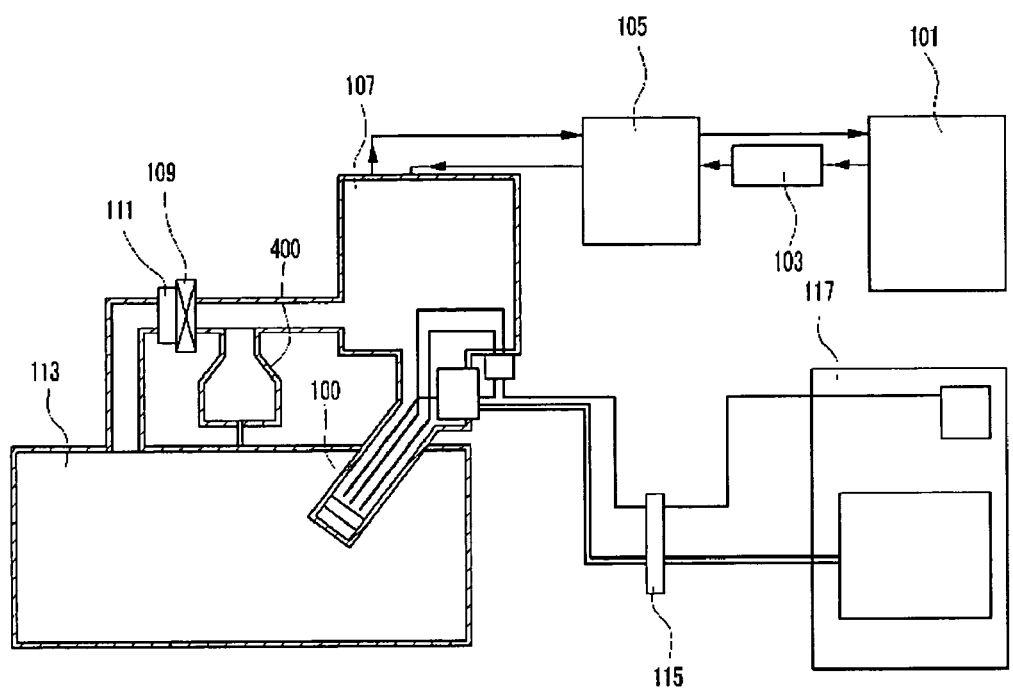
FIG. 2A is a schematic diagram of an example apparatus for analyzing a sample constructed in accordance with the teachings of the present invention.
Figure 2B:
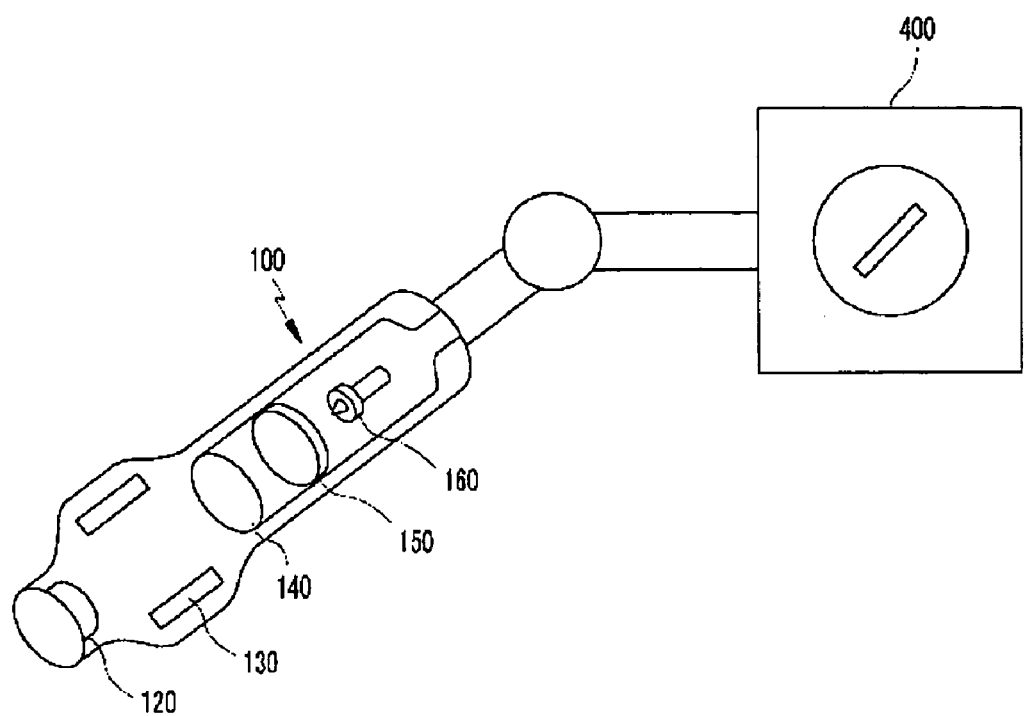
FIG. 2B is a schematic diagram of an example X-ray detector constructed in accordance with the teachings of the present invention.

FIG. 2A is a schematic diagram of an example apparatus constructed in accordance with the teachings of the invention for analyzing a sample. FIG. 2B is a schematic diagram of an example X-ray detector constructed in accordance with the teachings of the present invention.

Figure 1A:
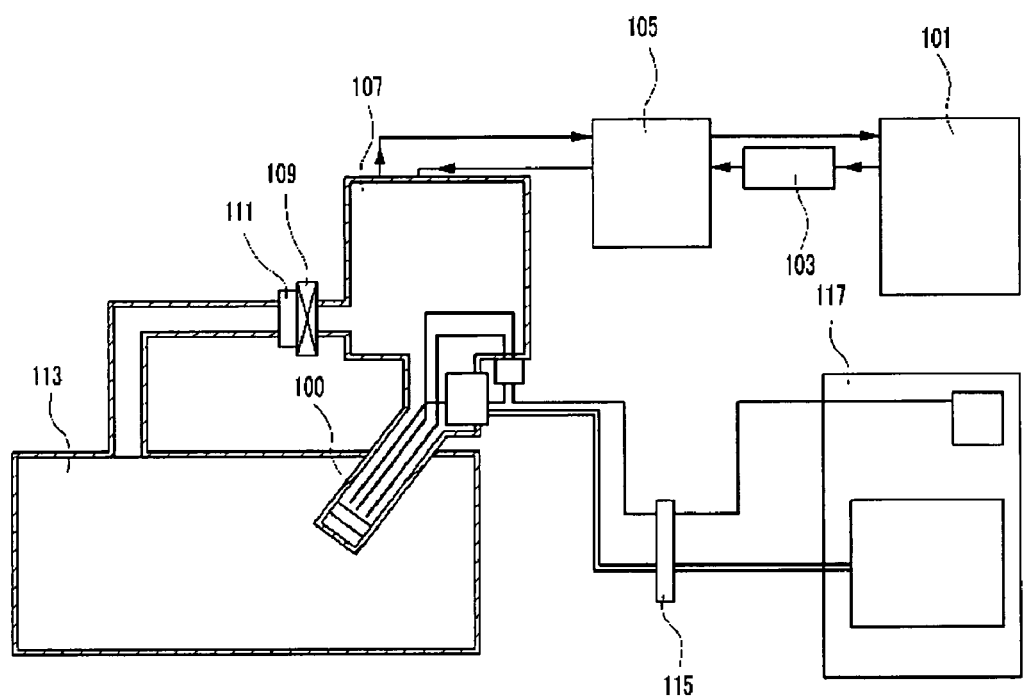
FIG. 1A is a schematic diagram of the inner structure of a conventional EDX.

Referring to FIG. 2A and FIG. 2B, the example apparatus for analyzing a sample includes a cooler head 107, a manual valve 109, an electrical isolator 111, a main chamber 113, a vacuum pump 400, an X-ray detector 100, an I/O panel 115, and an EDX rack 117, etc. Hereinafter, descriptions of some of the parts having the same or substantially the same structure as the like numbered parts shown in FIG. 1A will be omitted.

Figure 1B:
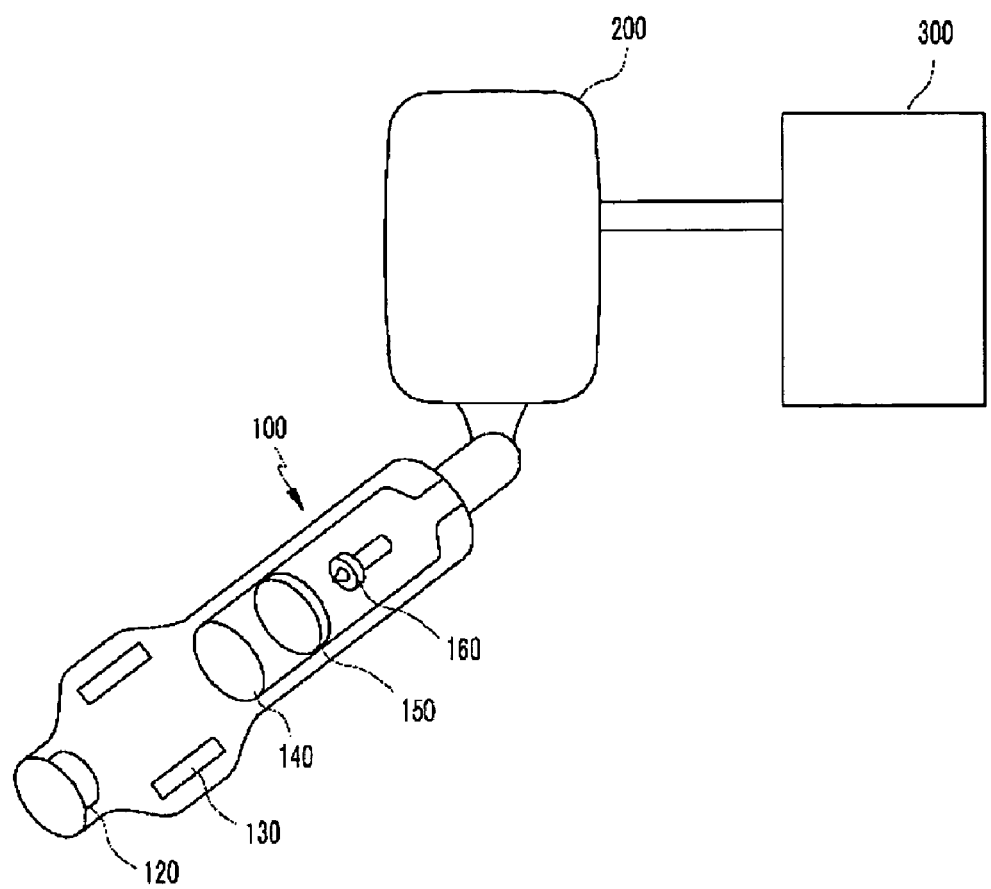
FIG. 1B is a schematic diagram of a conventional X-ray detector.

An example X-ray detecting device including the example X-ray detector 100 is provided with a vacuum pump 400 instead of the conventional cryostat 200. It is preferable that the vacuum pump be implemented as a TMP (Turbo Molecular Pump). The example X-ray detector 100 further includes an X-ray collimator 120 for collimating the X-rays, an electron trap 130 for eliminating electrons from the collimated X-rays, a window 140 for sealing to enable creation of a vacuum inside of the X-ray detector 100 and for transmitting the X-rays, a crystal 150 for generating an electric current corresponding to the energy of the X-rays, and a field effect transistor (FET) 160 for generating a voltage signal corresponding to the electric current generated by the crystal 150. Because the structural features and functions of the components 120, 130, 140, 150, and 160 are the same or substantially the same as the like numbered parts described in FIG. 1, they are not described in further detail. Instead, the interested reader is referred to the above description for a complete discussion of those components.

In the illustrated example, the X-ray detector 100 does not have a cryostat 200. Instead, the X-ray detector 100 has a vacuum pump such as a TMP (Turbo Molecular Pump). The vacuum pump 400 is used to create a vacuum inside of the X-ray detector. More precisely, the pump 400 is used to create a vacuum within a space sealed by the window 140 as an inner space including the crystal 150 and the FET 160. The vacuum pump 400 may be controlled by a control module 800 which will be described later with reference to FIG. 3. In this example, the conventional cryostat is not needed. Therefore, it is not necessary to supplement the liquid nitrogen and/or to replace the filter, and the maintenance cost is, therefore, decreased.

Figure 3:
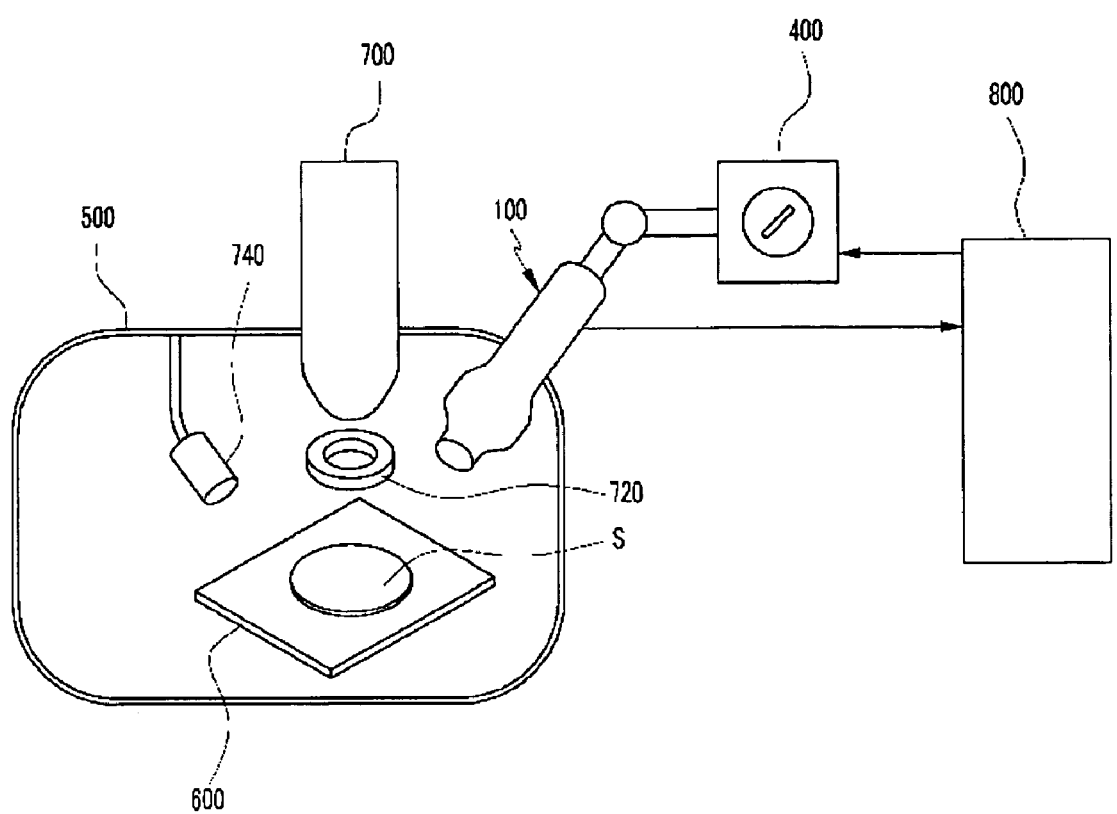
FIG. 3 is a schematic diagram of an example apparatus constructed in accordance with the teachings of the invention for analyzing a sample.

FIG. 3 is a schematic diagram of the structure of an example apparatus for analyzing a sample using the X-ray detector 100 described above. The illustrated example apparatus performs structural analysis with a scanning electron microscope 700 and compositional analysis with the X-ray detector 100 at the same time.

Various materials may be analyzed by such an apparatus. For instance, a semiconductor device may be used as an example sample S. Therefore, hereinafter the example apparatus of FIG. 3 will be described in connection with analyzing a semiconductor wafer S.

In the example shown in FIG. 3, the illustrated apparatus has a vacuumized chamber 500. A stage 600 supporting the sample S (for example, a semiconductor wafer), a portion of a scanning electron microscope 700 for performing structural analysis of the sample S, and a portion of an X-ray detector 100 for performing compositional analysis are disposed in this chamber 500. Although not shown in the drawings, the scanning electron microscope 700 includes an electron gun for emitting electrons and an electron lens system for scanning the emitted electrons on the sample S. The electrons emitted from the scanning electron microscope 700 collide with the sample S. Back-scattered electrons, secondary electrons, and characteristic X-rays are produced by this collision. A back-scattered electron detector 720 detects the back-scattered electrons. A secondary electron detector 740 detects the secondary electrons. An X-ray detector 100 detects the characteristic X-rays. The back-scattered electron detector 720 and the secondary electron detector 740 respectively create and output signals corresponding to the back-scattered electrons and the secondary electrons. A computer (not shown in the drawings) analyzes the signals to create a visual image corresponding to the surface structure of the sample S.

The X-ray detector 100 outputs a signal corresponding to the characteristic X-rays. A control module 800 or a computer connected to the control module 800 analyzes the chemical composition of the sample S. The chamber 500 is preferably maintained in a vacuum state of about 10.6~10.7 Torr to prevent an inflow of foreign particles, to efficiently induce the acceleration and emission of the electrons, and to improve the detecting sensitivity. Although not shown in the drawings, a vacuum pump, etc. are disposed so as to create this vacuum state. The X-ray detector 100 also has the vacuum pump 400 discussed above. The vacuum pump 400 causes the inside of the X-ray detector 100 to be maintained in a constant vacuum state. Preferably, the vacuum state of the X-ray detector 100 is the same or similar to that of the chamber 500.

As described above, the noise of the field effect transistor of the X-ray detector increases at an excessively low temperature. Therefore, a heater (not shown) is provided in the X-ray detector 100, and the temperature of the heater is controlled by the control module 800.

Hereinafter, an example manner of operating an example apparatus for analyzing a sample will be described.

First, a sample S (for example, a wafer) is disposed on a stage 600 in a chamber 500 of the apparatus. Next, the inside of the chamber 500 is vacuumized. A vacuum pump may be used to create this vacuum within the chamber 500, but the present disclosure is not limited thereto. After creating the vacuum within the chamber 500, the X-ray detector 100 is also vacuumized. As described above, the vacuum state of the X-ray detector 100 is preferably the same or similar to that of the chamber 500. To this end, it is preferable that a vacuum pump (which creates the vacuum inside of the chamber 500) and a vacuum pump (which creates the vacuum inside of the X-ray detector) are controlled in connection with each other. Next, electrons are emitted from the scanning electron microscope 700, and the emitted electrons collide with the surface of the sample S. As a result, back-scattered electrons, secondary electrons, and characteristic X-rays are emitted. The back-scattered electron detector 720 detects the back-scattered electrons, and the secondary electron detector 740 detects the secondary electrons. One or more signals reflecting this detection are sent to the computer, etc., to create a visual image corresponding to the surface of the sample. Simultaneously, the emitted X-rays are detected by the X-ray detector 100. A signal reflecting the detected X-rays is sent to the computer, etc., to be analyzed and displayed.

In the foregoing example X-ray detecting device and example apparatus for analyzing a sample using the X-ray detecting device, liquid nitrogen is not required because a cryostat is not used. As a result, there is no need to consume liquid nitrogen at the rate of about 1.1–1.3 liters a day common in prior art devices, and the cost of maintenance is, therefore, decreased.

In addition, since there is no need to use liquid nitrogen, the liquid nitrogen tank for supplementing the liquid nitrogen is not required. Therefore, the cost of providing the liquid nitrogen tank is eliminated, and the total volume of the apparatus decreases.

In addition, the cost of maintenance is also decreased because the filter is no longer required.

Further, since there is no need to perform the process of supplementing the liquid nitrogen and changing the filter, corresponding work is reduced and productivity is increased.

From the foregoing, persons of ordinary skill in the art will appreciate that X-ray detecting devices and apparatus for analyzing a sample using the X-ray detecting device have been disclosed which reduce the cost of supplying liquid nitrogen, reduce the volume of the apparatus, reduce the cost of supplies, and increase productivity.

A disclosed example X-ray detecting device having an X-ray detector for detecting X-rays emitted from a sample and outputting a converted signal reflecting the detected X-rays includes a collimator collimating the X-rays, an electron trap for removing electrons included in the collimated X-rays, a window for transmitting the X-rays and defining an interior space of the X-ray detector, a crystal to receive the X-rays which pass through the window and to generate a corresponding electric current, a field effect transistor to generate a voltage signal in response to the electric current which flows in the crystal, and a vacuum pump to create a vacuum within the interior of the X-ray detector enclosing the field effect transistor and the crystal, so as to suppress the noise of the crystal and the field effect transistor.

A disclosed example apparatus for analyzing a sample includes a vacuum chamber, a stage disposed in the chamber to hold the sample, a scanning electron microscope to perform structural analysis by bombarding electrons on a surface of the sample and detecting back-scattered electrons and secondary electrons, and an X-ray detector at least partially disposed in the chamber to perform compositional analysis by detecting X-rays created by the bombardment of the electrons, wherein the X-ray detector is provided with a vacuum pump to create a vacuum within an interior of the X-ray detector.

The vacuum pump may create a vacuum within the interior of the X-ray detector to be almost the same vacuum state as the chamber.

It is noted that this patent claims priority from Korean Patent Application Serial Number 10-2004-0115296, which was filed on Dec. 29, 2004, and is hereby incorporated by reference in its entirety.

Although certain example methods, apparatus and articles of manufacture have been described herein, the scope of coverage of this patent is not limited thereto. On the contrary, this patent covers all methods, apparatus and articles of manufacture fairly falling within the scope of the appended claims either literally or under the doctrine of equivalents.

What is claimed is:

1. An X-ray detecting device having an X-ray detector to detect X-rays emitted from a sample, the X-ray detecting device comprising:

a collimator to collimate X-rays emitted from the sample;

an electron trap to remove some of the electrons included in the collimated X-rays;

a window to transmit the X-rays and defining an interior space of the X-ray detector;

a crystal to receive the X-rays which pass through the window and to generate a corresponding electric current;

a field effect transistor to generate a signal in response to the electric current associated with the crystal; and a vacuum pump to create a vacuum within the interior of the X-ray detector enclosing the field effect transistor and the crystal to suppress noise associated with at least one of the crystal or the field effect transistor, wherein the vacuum pump comprises a turbo molecular pump (TMP).

2. An apparatus comprising:

a chamber containing a vacuum;

a stage disposed in the chamber to hold a sample;

a scanning electron microscope to perform structural analysis, the scanning electron microscope being positioned to bombard electrons on a surface of the sample and to detect back-scattered electrons and secondary electrons; and an X-ray detector to perform compositional analysis, the X-ray detector comprising the X-ray detector of claim 1 and being at least partially disposed in the chamber to detect X-rays created by the bombardment of the electrons.

3. An apparatus as defined in claim 2, wherein the vacuum created within the interior of the X-ray detector is substantially the same as the vacuum within the chamber.

* * * * *